United States Patent [19]

Kessler

[11] Patent Number: 5,370,815
[45] Date of Patent: Dec. 6, 1994

[54] VISCOUS EPIDERMAL CLEANER AND DISINFECTANT

[76] Inventor: Jack H. Kessler, 122 Boston Post Rd., Sudbury, Mass. 01776

[21] Appl. No.: 59,956

[22] Filed: May 13, 1993

Related U.S. Application Data

[63] Continuation-in-part of Ser. No. 681,447, Apr. 4, 1992, Pat. No. 5,227,161, which is a continuation of Ser. No. 515,332, Apr. 27, 1990, which is a continuation of Ser. No. 240,212, Sep. 6, 1988.

[30]  Foreign Application Priority Data

Jun. 25, 1990 [EP]  European Pat. Off. ........ 90112045.9

[51] Int. Cl.$^5$ ...................... A61K 31/23; A61C 13/00
[52] U.S. Cl. ................. 252/106; 252/DIG. 5; 422/37; 424/54.4
[58] Field of Search ................. 252/100, DIG. 5, 106; 422/37; 424/94.4

[56]  References Cited

U.S. PATENT DOCUMENTS

| | | | |
|---|---|---|---|
| 3,282,777 | 11/1966 | Ceriotti | 424/671 |
| 3,728,449 | 4/1973 | Contor et al. | 424/671 |
| 3,966,090 | 6/1976 | Prussin et al. | 222/94 |
| 4,012,504 | 3/1977 | Eckols | 424/667 |
| 4,067,967 | 1/1978 | Prince | 424/667 |
| 4,140,766 | 2/1979 | Kalogris | 424/667 |
| 4,414,127 | 11/1983 | Fu | 252/95 |
| 4,485,029 | 11/1984 | Kato et al. | 252/106 |
| 4,588,586 | 5/1986 | Kessler et al. | 424/94 |
| 4,670,178 | 6/1987 | Huth | 252/95 |
| 4,808,328 | 2/1989 | Flohr | 424/667 |
| 4,814,109 | 3/1989 | Wittpenn, Jr. et al. | 252/547 |
| 4,935,248 | 6/1990 | Witken | 424/671 |
| 5,055,287 | 10/1991 | Kessler | 424/669 |
| 5,169,455 | 12/1992 | Kessler | 424/613 |

FOREIGN PATENT DOCUMENTS 0307376  3/1989  European Pat. Off. .

OTHER PUBLICATIONS

Chem Abstracts vol. 104 Mar. 31, 1986 No. 13.
Chem Abstracts vol. 68 Feb. 12, 1968, No. 7.

Primary Examiner—Paul Lieberman
Assistant Examiner—Necholus Ogden
Attorney, Agent, or Firm—E. Lieberstein

[57]  ABSTRACT

This invention relates to a viscous epidermal cleaner and disinfectant using peroxidase, peroxide, an iodide compound, surfactants and buffering agents to control the pH when admixed in water for forming a viscous composition with a pH between 3.0 and 6.5 and a viscosity of not less than 1.2 centipoise. The active components are maintained inactive until admixed in a defined proportion with water. The pH at which the peroxidase is stored is between 7.0 and 9.0 and the pH of the admixture of the active components is between 3.0 and 6.5. Alternatively, all of the components of this application can be shipped as dry powders or tablets and dissolved prior to use to yield a viscous aqueous environment that will be applied to the epidermis with no further dilution.

12 Claims, 1 Drawing Sheet

LOG REDUCTION OF ASPERGILLUS FUMIGATIS vs pH pH of Disinfecting Reaction
(Component A + Component B + 0.3 mol/L buffer + water)

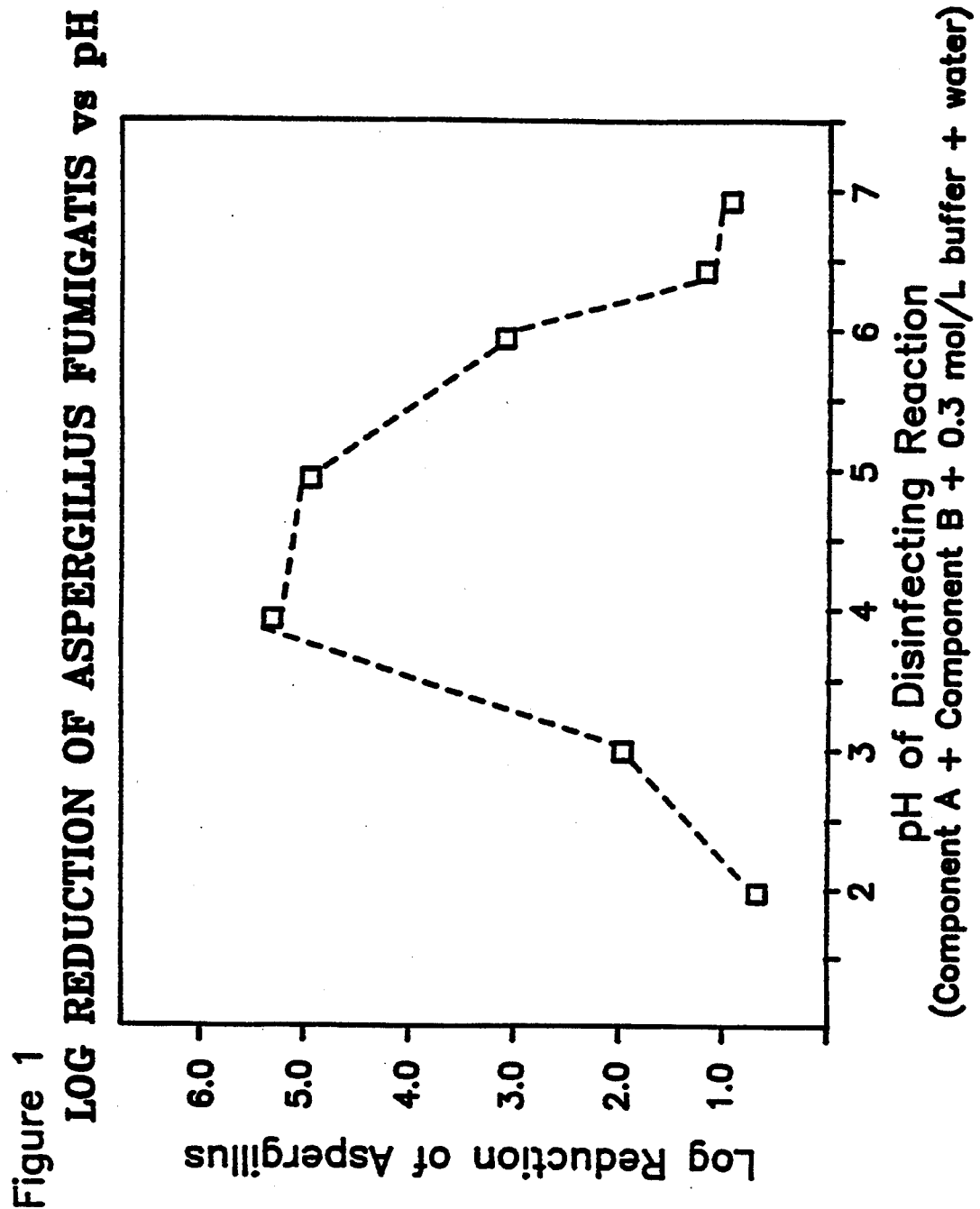
Figure 1 LOG REDUCTION OF ASPERGILLUS FUMIGATIS vs pH

VISCOUS EPIDERMAL CLEANER AND DISINFECTANT

FIELD

This invention is a continuation in part of U.S. patent application Ser. No. 07/681,447 filed Apr. 4, 1992 which in turn is a continuation of Ser. No. 07/5 15,332 filed Apr. 27, 1990 which in turn is a continuation of Ser. No. 07/240,212 filed Sep. 6, 1988. This invention relates to a disinfecting epidermal cleaner which incorporates peroxidase, a source of peroxide and iodide at a controlled pH to cause antiseptic disinfection in the presence of water. The epidermal cleaner is comprised of a viscous emollient formulation with a high concentration of surface active agents.

INTRODUCTION

Liquid epidermal cleaners contain a variety of surface active agents which perform several functions. These compositions generally contain surfactants, lathering agent(s), thickening agents, humectants and foam stabilizers. A disinfecting epidermal cleaner also contains antiseptic agents in combination with many or all of the preceding agents. The most commonly used antiseptic agents in disinfecting soaps are povidine-iodine (Disadine), chlorhexidine (Hibiscrub) and hexachlorophene (Phisohex).

The principle differences between conventional disinfecting soap compositions and the disinfecting epidermal cleaner of the present invention are (1) none of the components of this invention acting alone contribute a practical antiseptic activity to the product of this patent, (2) the inceptive bactericidal agent generated during the chemistry of this application is the enzyme generated free radical of iodide (or by-products) which is a fundamentally different chemistry from that of the antiseptic agents previously used in epidermal cleaners, and (3) the antiseptic activity of the disinfecting epidermal cleaner of the present invention does not cause irritation to the epidermis nor is it organoleptically aversive. The formulation of an emollient non-irritating antiseptic epidermal cleaner is only possible if the active antiseptic agents do not cause discomfort and are able to be formulated in an organoleptically unobjectionable medium.

The disinfecting epidermal cleaner as described in this specification is formulated to work upon admixture in an aqueous medium. Preferably a defined volume of water is admixed with the disinfecting components such that the individual components are diluted by 50 to 1000% upon use. That is, the concentration of the disinfecting epidermal cleaner of this application is designed to be diluted in water prior to use. Alternatively, the components of this application can be shipped as dry powders and dissolved prior to use to yield a viscous aqueous environment that will be applied to the epidermis with no further dilution.

BACKGROUND

The essential constituents in commercial epidermal cleaning compositions are an antiseptic agent and a surfactant; however the final composition should exhibit high foaming, good water solubility, adequate detergency and acceptable organoleptic characteristics. Formulation of epidermal cleaning compositions containing conventional antiseptic agents has been problematical due to incompatibilities resulting from (1) destruction of the activity of said antiseptic agents, (2) phase incompatibility of said antiseptic agents, (3) long-term stability of said antiseptic agents in highly detergent compositions, and (4) achieving acceptable organoleptic properties. This application discloses the use of a composition containing peroxidase, peroxide and iodide in a prescribed formulation suitable for use as an antiseptic agent to form a disinfecting epidermal cleaner which does not suffer from the above incompatibilities.

For the peroxidase based composition of the subject invention to provide antiseptic activity in an epidermal cleaner the following must be achieved: (1) the maintenance of enzymatic activity, (2) the maintenance of substrate (peroxide and iodide) concentrations within a defined range, (3) the absence of molecules or reaction by-products which meaningfully compete with iodide or peroxide for the active site of the enzyme, (4) the diffusion of the nascent bactericidal iodide radical (or by-product) from the enzyme's active site to targeted organisms, and (5) the absence of vitiating interactions between the bactericidal iodide free radicals (or by-products) and other components in the environment. The possibility of creating an effectual disinfecting epidermal cleaner whose biocidal ingredients are comprised of peroxidase, peroxide and iodide, can only be accomplished if the five requirements listed above are substantially met.

It is known from Kessler (U.S. Pat. Nos. 4,476,108, 4,588,586 and 4,473,550), Orndoff (U.S. Pat. No. 4,370,199) and Montgomery (U.S. Pat. No. 4,576,817) that a composition of peroxidase, peroxide and a source of donor molecules will form a bactericide in an aqueous non-viscous solution. The source of donor molecules must be capable of dissolving in water in order for the system to function as a disinfectant. For purposes of the present invention non-viscous means a viscosity of less than 1.2 centipoises. The disinfecting applications described in the above identified patents take place either in a totally aqueous environment or upon a meaningful dilution or dissolution (greater than 10 fold) of a formulation to form a substantially aqueous environment. None of the previous applications involve disinfecting environments which are viscous and/or contain high concentrations of surface active agents required for a useful disinfecting epidermal cleaner.

The present invention may be used to disinfect any epidermal surface on either a human or animal. In fact the present invention is particularly suited to the treatment of bovine mastitis.

The viscosity of commercial liquid soap cleaners am often at least about 5 centipoises and are typically above 20 centipoises and sometimes greater than 100 centipoises. The viscosity inherent to liquid epidermal cleaning compositions will reduce the diffusion of molecules relative to that in a substantially aqueous environment. The short-lived lifetime of the free radical (or by-products) generated by the removal of an electron from a donor molecules imposes a constraint upon a system which requires an enzymatic reaction to occur between peroxidase, peroxide and donor molecules. The free radicals (or by-products) generated at active site of peroxidase must have enough time to diffuse to their ultimate site of action in order for the system to be effective. The diffusion coefficient, which is proportional to the rate of motion of a molecule in a matrix, is inversely proportional to the viscosity of a matrix. Accordingly, the viscosity inherent in the high concentrations of surface active agents, including; unsaturated fatty-acids, could be expected to decrease or eliminate the disinfecting ability of this system.

In traditional cold chemical disinfectants are used by forming a homogeneous solution/suspension of the disinfecting chemical provides a known concentration of active species throughout the environment. That is, with traditional cold disinfectants there exists a known evenly distributed concentration of stable disinfecting agents at the outset of a disinfection regime. These disinfecting agents are free to diffuse through solution and contact pathogenic organisms of interest. Through trial and error, the concentration of the chemical disinfecting agents is chosen such that there are enough molecules of the disinfectant to contact pathogen organisms in the desired time frame to effect the desired biocidal activity.

Unlike traditional cold chemical disinfectants, the peroxidase system of Kessler relies upon an enzymatic reaction to generate disinfecting species. The full disinfecting cycle consists of the following reactions: (1) hydrogen peroxide must diffuse to the active site of the enzyme; (2) a molecule of water must diffuse from the active site of the enzyme; (3) an iodide molecule must diffuse to the active site of the enzyme; (4) the enzymatic by-product of iodide oxidation must diffuse from the active site of the enzyme; (5) another iodide molecule must diffuse to the active site of the enzyme; (6) a water molecule must diffuse from the active site of the enzyme; (7) an active intermediate must diffuse from the active site of the enzyme; and (8) the active intermediate must survive long enough to collide with a pathogen of interest. The Stokes-Einstein relationship defines the overall diffusion of a molecule as a function of viscosity. This equation indicates that diffusion is inversely related to viscosity. Thus for every 10% increase in viscosity the rate of diffusion of a species in solution is slowed by a factor of 9.1%.

Moreover, unlike traditional chemical disinfectants, the peroxidase system of Kessler relies upon a series of chemical reactions with each of these reactions expected to be slowed by an increase in viscosity. That is, a reduction in the rate of diffusion will effect each of the individual reaction steps in Kessler which comprise a full disinfecting cycle. In particular, a significant increase in viscosity would be reasonably anticipated to have a significantly effect on step 7 (the active intermediate must diffuse from the enzyme) and step 8 (the active intermediate must collide with a pathogen) which are critical for disinfection. The reason that these steps would be anticipated to be especially sensitive to a reduction in their diffusion associated rate constant is that the active disinfecting agent is a by-product of the enzymatic reaction generated within the active site of the enzyme a significant distance from pathogens that are the desired site of activity. Thus it is reasonably inferred that the biocidal species might not survive long enough to collide with pathogens.

In Karo (U.S. Pat. No. 4,485,029) a composition is taught for cleaning, disinfecting and preserving contact lens comprised of glyceryl monolaurate in combination with antimicrobials, organic surfactants, alkali metals, adjuvants and buffer. This type of product includes surface active agents but not in a viscous environment since this would obstruct cleaning and potentiate the possibility for eye irritation. The viscosity of all of the formulations taught in Karo lie within the viscosity range between 1.010 to 1.060 centipoise.

It has been discovered in accordance with the present invention that a composition of peroxidase, peroxide and a source of a donor molecule can form an antiseptic agent for use in an aqueous epidermal cleaner under conditions of high viscosity by using iodide as the donor molecule and by controlling the pH of the aqueous composition between a pH of 3.0 to 6.5. Viscosity is a critical element of this invention since it is a required property of many products like certain soaps and bovine teat disinfectants. For purposes of the present invention, the relative viscosity of a disinfecting composition can be measured using an Ostwald viscometer by measuring the amount of time it takes for the liquid level to fall through a defined length of a capillary tube. The relative viscosity of a formulation is then calculated by comparing the time required for the formulation to fall divided by the time required for distilled water to fall the equivalent distance. The epidermal cleaner may have a high concentration of surface active agents with a viscosity above 1.2 centipoises to assure satisfactory cleaning simultaneously with disinfection. The epidermal cleaner of the present invention broadly comprises a surface active agent, an antiseptic agent including peroxidase, a source of peroxide, and an iodide compound in combination with a buffering system to cause a pH of between 3.0 and 6.5 when the cleaner is diluted with water over a dilution range of about 10 to 1 water to cleaner. The subject invention contemplates the use of any buffering system in conjunction with or without an inert carder to cause equilibration of the composition in water with a pH in the final admixture of between 3.0 and 6.5 over a wide dilution range.

BRIEF DESCRIPTION OF THE FIGURE

FIG. 1 shows the reduction in viable *Aspergillus fumigatis* in a liquid soap formulation as a function of pH over a five minute time period.

DETAILED DESCRIPTION OF THE INVENTION

The disinfecting epidermal cleaner of the present invention comprises a surface active agent, an antiseptic agent formed from the combination of peroxidase, a source of peroxide, a source of iodide, and a buffering system to establish a controlled pH of between 3.0 to 6.5 when the epidermal cleaner is admixed with water. Peroxidase and iodide are stored in a buffered environment at a pH between 7.0 and 9.0. The buffering agents of the peroxidase component are at a concentration such that upon admixture with water and the buffered peroxide component, the pH of the final admixture is between 3.0 and 6.5. In practice this usually means that the concentration of the buffering agents in the peroxidase component is significantly lower than the concentration of pH controlling agents in the peroxide component; that is, the peroxidase containing component is weakly buffered. Peroxide is stored in a strongly buffered environment at a pH between 3.0 and 6.5. Alternatively, all of the components of this application can be shipped as dry powders or tablets and dissolved prior to use to yield a viscous aqueous environment that will be applied to the epidermis with no further dilution. This patent discloses the ability of a peroxidase based disinfecting epidermal cleaner to work with a variety of known emollient and detergent agents at viscosity levels above 1.2 centipoise.

Controlling the pH of the final reaction mixture is a critically important aspect of this invention when the source of donor molecules is an iodide salt. The iodide donor molecule at low pH revels apears to overcome constraints imposed by viscosity. As can be seen in FIG. 1, the disinfecting activity of the epidermal epidermal cleaner is related to the pH in which the disinfecting reaction occurs. By controlling the pH of the reaction once all of the components have been admixed with water, the utility of the admixture is meaningfully enhanced. The disinfecting reaction takes place significantly more rapidly as the pH decreases from a pH of 7.0 to a pH 4.0. The preferred pH range is between 6.0 and 3.0 with an optimum pH range of 4.0 to 5.5. Below a pH of 3.0 the reaction appears to be less effective.

The surface active agents of the disinfecting epidermal cleaner of this invention consist of a class of molecules comprised or anionic, cationic, zwitterionic, nonionic and ampholytic surface active agents. These molecules comprise a principal ingredient of presently used liquid soap and handcream formulations. Said molecules include sodium lauryl sulfate, lithium lauryl sulfate, alkyl benzenesulfonates, alkane sulfonates, alkene sulfonates, Tween 20-polyoxyethylene sorbitan monolaurate, Tween 100, alkyl sulphates, alkyl ether sulphates, polyoxyethylene condensation products or primary and secondary alcohols, fatty acid amides, block polymers of ethylene oxide and propylene oxide, myristic acid, lauric acid, capric acid, caprylic acid, coconut and palm kernel fatty acids, polyethoxylated glucosides and esters, hydroxy ethyl cellulose, hydroxy propyl quar, N-acyl-sarconsinates, sodium-N-acyl-N-methyl taurates, sodium cocoylisothioate, hydroxypropyl guar gum, amidopropyl betaines, and polyethylene glycol derivitives.

The donor molecule of this invention is iodide. Suitable sources of iodide for this invention include sodium iodide and potassium iodide as well as other salts of iodide. Any source of iodide or iodide compound which yields iodide ions upon dissolution in water, without yielding other deleterious effects to the activity of the system, is suitable for this application. The simple salts of iodide are preferred and have the advantage of being inexpensive. Additionally, they have a long shelf life both in solid and liquid form.

The peroxidase enzyme of this invention is identified by the International Union of Biochemistry and the International Union of Pure and Applied Chemistry by the Enzyme Commission identification No. E.C. 1.11.1.7. Peroxidase can be obtained from a wide variety of sources. The least expensive and most robust peroxidase suitable for this application is horseradish peroxidase. Commercially obtained peroxidase comes lyophilized as a dry powder which can then be admixed in a suitable carrier.

The preferred oxidant of this invention is hydrogen peroxide. Any material which acts as a source of peroxide when admixed in water is suitable for the present invention. This "source of peroxide" for purposes of the present invention means any material which can serve as precursors for hydrogen peroxide including metal peroxides, percarbonates, persulphates, perphosphates, peroxyesters, urea peroxide, peroxyacids, alkylperoxides, acylperoxides and perborates. Alternatively methyl peroxide can be formulated in the product. Mixtures of two or more of these substances can also be used.

The peroxidase containing component of the disinfecting epidermal cleaner of this application preferably includes a carder such as glycerol although other carriers and combinations of carriers are possible. To maximize the shelf-life of the product it is necessary to include iodide compound in the peroxidase component of this invention and not to admix iodide in the peroxide containing component. Immediately prior to use, a defined volume of the peroxidase/iodide containing component and the peroxide/surfactant containing component are combined with water to form the active disinfecting epidermal cleaner of the instant invention. The formulations will function over a range of ratios of exogenously added water to peroxidase/iodide-peroxide/surfactant containing components. This ratio is based on volume to volume comparisons. The volume of water added divided by the sum of the volumes of the peroxidase/iodide-peroxide/surfactant containing components is between 0.5 and 10. These considerations are obviated if all of the components of this application are shipped as dry powders or tablets and dissolved prior to use to yield a viscous aqueous environment for application to the epidermis with no further dilution.

There are certain types of products such as bovine teat dip products to prevent mastitis, and products for topical application which are ordinarily not diluted prior to use. Formulations for these products can be shipped as powders or tablets or combinations of aqueous based components and powders or tablets. All components will be combined prior to use to yield a disinfecting environment of high viscosity prior to use. This product configuration has the advantage of improved shelf-life but requires greater effort and compliance on the part of the end-user.

The peroxidase containing component of this invention consists essentially of water, carrier, the enzyme peroxidase, and a suitable buffering agent. The iodide salt is preferably added to the peroxidase component. The buffering agent tris(hydroxymethyl)aminomethane at a final concentration between 1 and 10 mM at a pH between 7.0 and 9.0 and a calcium ion concentration between 2 and 25 mM is preferable. Sodium phosphate cannot be used either as the buffering agent or as an additive of the peroxidase containing component since it binds calcium and will, as a result, dramatically reduce the shelf-life of the product. Any compound or mixture of compounds which binds or sequesters calcium cannot be added to the peroxidase containing component.

The preferred carriers for the peroxidase containing component are sucrose, ethylene glycol, glycerol and other polyhydroxylated alkanes in which peroxidase has good stability. Carriers are present at a concentration of 5 to 45% w/v depending upon the selection of carrier(s) since different carriers have distinct properties. The preferred iodide salts for the peroxidase containing component is sodium iodide and potassium iodide. The concentration of iodide in the peroxidase containing component is between 0.5 and 8.0 mg/ml and preferably between 1.0 and 4 mg/ml when the peroxidase component is diluted as described above prior to use.

The second component of the disinfecting epidermal cleaner of this patent contains peroxide in a broad concentration between 0.001% and 1.0% weight to volume basis in the detergent based carder component and in a preferred range of 0.01 to 0.10%. If the product is shipped as a powder and dissolved prior to use, the preferred concentration of hydrogen peroxide in solution instantaneously after dissolution is between 0.01 and 0.1%. Iodide may not be combined in this component as this will reduce the shelf life of the final product as iodide is known to be unstable at an acidic pH. The preferred detergent agents are sodium lauryl sulfate and lithium lauryl sulfate although many other detergents can be used and can be combined for admixture into the peroxide component of the disinfecting epidermal cleaner of this application. The concentration of the detergent depends upon which compound or mixtures of compounds are used and what the intended use is. Typically the concentration of detergents is between 5 and 25 % of the peroxide formulation, although some formulations may have very low concentrations of detergent. The pH of the peroxide containing component is carefully controlled so that it is between pH 3.0 and 6.5. The concentration of buffer used in the peroxide containing component is preferably between 0.100 and 1.0 molar in the peroxide containing component. Sodium phosphate is the buffer of choice for the peroxide containing component since its cost is low; however, the concentration of buffering component will vary depending upon which buffer is used.

The critical aspect of the buffering of the peroxide containing component is that the buffer must be concentrated enough to control the pH of the final admixture within a pH range between a pH 3.0 and 6.5 when admixed with defined portions of the peroxidase/iodide component and peroxide component and portions of water which vary from 50 percent to ten times the combined volumes of the peroxidase/iodide and peroxide components.

The peroxide containing component of the disinfecting epidermal cleaner of this application can contain a variety of nonessential optional ingredients suitable for rendering such compositions more desirable. Such common ingredients are familiar to those skilled in the art and include preservatives, viscosity modifiers, coloring agents, pH controlling agents, suspending agents, sequestering agents, perfumes and opacifiers. However, no sequestering agents or any agent which bind calcium can be included in the peroxidase containing component. Agents commonly used as preservatives which are compatible with the chemistry of this application include benzyl alcohol, methyl paraben, sorbic acid. Carboxymethyl cellulose, ethylcellulose, polyvinyl alcohol and guar gum derivatives are commonly used as thickeners and can be used with the formulations of this application. Phosphoric acid, sodium phosphate, sodium hydroxide, tris-(hydroxymethyl) aminomethane as pH controlling agents. Magnesium/aluminum silicate as suspending agents and ethylenediaminetetraacetic acid as a sequestering agent.

EXAMPLES

Example 1

Component A, the peroxidase containing component, consisted of 0.4 mg/ml of Sigma Type I peroxidase, 4 mg/ml acetylated BSA, 2 mg/ml sodium iodide, 0.2 mg/ml calcium chloride, 1 mM tris-(hydroxymethyl) aminomethane (pH 7.2), and 20% glycerol.

Component B, the peroxide containing component, consisted of 0.0038% hydrogen peroxide, 2.5% sodium lauryl sulfate, 0.125 mg/ml ethylenediaminetetraacetic and 0.125 mg/ml of sorbic acid. Four ml of component B was added to 1 ml of several phosphate buffers each of which was 0.4 molar. The pH of the 0.4 molar phosphate buffers was 4.0, 4.5, 5.5 and 6.5.

Cultures of *Listeria selegeri*, *E. coli*, and *Salmonella typhimurium* were spun down in a clinical centrifuge and washed in normal saline. Equal volumes of component A (1 ml) and component B (1 ml) were added to 1 ml of these bacterial suspensions and mixed. Aliquots were withdrawn every 20 seconds and diluted in 10 mg/ml sodium fluoride. Serial dilutions of each time point were made and the CFU per ml was determined. The rate of inactivation in viable organisms per unit time was calculated by taking the logarithm of the ratio of the number of viable organisms at the start of the reaction divided by the number of organisms which were viable at the end of the reaction and dividing this ratio by the time of the reaction.

| *Listeria selegeri* | | | | |
|---|---|---|---|---|
| 4.0 | 4.5 | 5.5 | 6.5 | pH |
| 0.16 | 0.092 | 0.076 | 0.059 | Rate of Inactivation |
| *E. coli* | | | | |
| 4.0 | 4.5 | 5.5 | 6.5 | pH |
| 0.12 | 0.11 | 0.087 | 0.077 | Rate of Inactivation |
| *Salmonella typhimurium* | | | | |
| 4.0 | 4.5 | 5.5 | 6.5 | pH |
| 0.15 | 0.10 | 0.093 | 0.077 | Rate of Inactivation |

Each of the organisms were inactivated. The lower pH values yielded a more rapid inactivation. When the concentration of sodium lauryl sulfate was increased 10 fold, all of the organisms were inactivated within 40 seconds.

Example 2

Component A, the peroxidase containing component, consisted of 1.0 mg/ml of Sigma Type I peroxidase, 30% sucrose, 6 mg/ml sodium iodide, 1.0 mg/ml calcium chloride, 5 mM tris-(hydroxymethyl)aminomethane (pH 7.5), and 4mg/ml sodium chloride. Component B, the peroxide containing component, consisted of 0.0030% hydrogen peroxide, 1.0% cetyl alcohol, and 1.0% Brij-35. Four ml of component B was added to 1 ml of several phosphate buffers each of which was 0.3 molar. The pH of the 0.3M phosphate buffers was 4.0, 4.5, 5.5 and 6.5.

Cultures of *Staphlococcus aureus*, *Staphlococcus epidermitis*, and *Salmonella typhimurium* and *Listeria selegeri* were spun down in a clinical centrifuge and washed in normal saline. Equal volumes of component A (1 ml) and component B (1 ml) were added to 1 ml of these bacterial suspensions and mixed. Aliquots were withdrawn every 20 seconds and diluted in 10 mg/ml sodium fluoride. Serial dilutions of each time point were made and the CFU per ml was determined. The rate of inactivation of viable organisms per unit time was calculated by taking the logarithm of the ratio of the number of viable organisms at the start of the reaction divided by the number of organisms which were viable at the end of the reaction and dividing this ratio by the time of the reaction. Each of the organisms were inactivated. The lower pH values yielded a more rapid inactivation. When the concentration of Brij-35 and cetyl alcohol was increased tenfold, the rate of inactivation at a pH of 6.0 was increased.

| *Listeria monocytogenes* | | | | |
|---|---|---|---|---|
| 3.5 | 4.5 | 5.5 | 6.5 | pH |
| 0.22 | 0.077 | 0.055 | 0.003 | Rate of Inactivation |
| *S. aureus* | | | | |
| 3.5 | 4.5 | 5.5 | 6.5 | pH |
| 0.006 | 0.003 | 0.002 | 0.002 | Rate of Inactivation |

| Salmonella typhimurium | | | | |
|---|---|---|---|---|
| 3.5 | 4.5 | 5.5 | 6.5 | pH |
| 0.13 | 0.06 | 0.045 | 0.034 | Rate of Inactivation |
| S. epidermidis | | | | |
| 3.5 | 4.5 | 5.5 | 6.5 | pH |
| 0.125 | 0.088 | 0.043 | 0.030 | Rate of Inactivation |

Example 3

The effect of pH between 2.0 and 7.0 on the inactivation of *Aspergillus fumigatis* with a disinfecting epidermal epidermal cleaner was examined. The peroxidase component (component A) contained 1.0 mg/ml of sodium iodide, 20.0 percent glycerol, 5.0 mg/ml of sodium chloride, 1.1 mg/ml of calcium chloride, 0.5 mg/ml of peroxidase (Sigma Type I) in 10 mM tris-hydroxymethyl)aminomethane. The peroxide component (component B) contained 0.03 percent hydrogen peroxide, 1.0 mg/ml of ethylenedimninetetraacetic, and 1.8 percent of sodium-lauryl-sulfate in water. Immediately prior to use, component B was mixed with 0.20 mol/L buffers which had been equilibrated at the desired pH values. For a pH value in the disinfecting admixture of 7.0, 6.5, and 6.0, sodium phosphate was used as the buffer for mixture with component B. For a pH value in the disinfecting admixture of 5.0, and 4.0, citric acid—sodium phthalate was used as the buffer for mixture with component B. For a pH value in the disinfecting admixture of 3.0 and 2.0, phthalic acid—sodium phthalate was used as the buffer for mixture with component B.

*Aspergillus fumigatis* in 0.125 ml (4,000,000 CFU) was added to 0.50 ml of component A. A one part to one part mixture of component B with each buffer was added (0.50 ml) to 2.0 ml of water and mixed. These two mixtures were added and incubated at room temperature for 5 minutes. Samples were removed (0.10 ml) and diluted into 0.30 mol/L with respect to sodium fluoride. This suspension and serial dilutions of this mixture (0.10 ml) were spread on Sabouraud dextrose/agar plates and incubated for three days at 42 degrees centigrade. The log reduction over the five minute time period was calculated (FIG. 1) by subtracting the logarithm of the number of viable organisms at the end of the reaction from the logarithm of the number of organisms at the start of the reaction which were viable at the end of the reaction.

| Aspergillus fumigatis Log reduction per 5 Minutes | | | | | | | |
|---|---|---|---|---|---|---|---|
| pH | | 2.0 | 3.0 | 4.0 | 5.0 | 6.0 | 6.5 | 7.0 |
| log Reduction | 1.3 | 2.0 | 5.4 | 5.0 | 3.2 | 1.2 | 1.0 |

*Aspergillus fumigatis* were inactivated at each pH value. The lower pH values yielded a greater degree of inactivation. The inactivation at pH 2.0 was not as rapid as the inactivation at 3.0 or 4.0. It is likely that the enzyme is inactivated at this pH value. When the concentration of sodium lauryl-sulfate was increased 10 fold there was a 6 log reduction at a pH of 5.0.

Experiment 4

The intent of this experiment is to determine the relationship between viscosity and the rate of inactivation of *Bacillus stearothermophilus* (BST). Glucose was used to incrementally increase the relative viscosity from 1.0 to 1.85 cp. In addition, once the rate of inactivation of BST was determined, the pH of the reaction buffer was varied to determine the upper pH limit at which BST was completely inactivated in 60 minutes.

Viscosity Measurements

The viscosity of these formulations were measured in an Ostwald viscometer by determining the amount of time it takes for the liquid level to fall through a defined length of a capillary tube with an inner diameter of 5 min. The relative viscosity of a formulation was calculated by comparing the time required for the formulation to fall divided by the time required for distilled water to fall the equivalent distance.

Microbiology Protocol

1. Organisms: *B. stearothermophilus* (ATCC 12980).
2. Chemistry Formulation: Buffer is 0.10 molar citrate-carbonate, pH 4.0; hydrogen peroxide at a final concentration of 552 ppm; horseradish peroxidase at a final concentration of 0.005 mg/ml; and sodium iodide at a final concentration of 2.0 mg/ml; glucose at the indicated concentration.
3. Neutralizing media: Trypticase Soy Broth (TSB) containing 0.1% sodium thiosulfate. TSB has a final pH of 7.3 and is comprised of 17 grams pancreatic digest of casein; 3 grams papaic digest of soy meal; 5 grams sodium chloride; 2.5 grams glucose; 2.5 grams potassium phosphate dibasic; 1000 ml of distilled water.
4. Subculture media: Trypticase Soy Broth (TSB).
5. Treatment Conditions: At T=0 minutes. 0.7 ml of a $3.0\times10^8$ cfu/ml spore suspension was added into 10 ml of disinfectant solution to yield an initial population of $2\times10^7$ cfu/ml. At time intervals, 0.5 ml aliquots of the reaction mixture were aseptically removed and immediately transferred to 9.5 ml neutralizing media. The sample was sonicated in a jewelry bath sonicator for 15 minutes and then 1 ml of each of the inactivated reaction tubes was transferred into 10 ml of TSB. One tube was saved for plating to determine the number of viable organisms per ml.
6. D-values: Sample tubes containing inactivated reaction mixture were incubated up to 7 days at 55° C.±1° C. and observed for typical growth, followed by secondary inoculation with <100 cfu of challenge organism to verity that organisms are capable of growth in the media (verify neutralization). The fraction of positive tubes ($n_p$) was recorded and D-values (log reduction of organism/minute) were calculated using the Stumbo equation:

$$D\text{-value}=time\ [\log(N_o n^t)-\log(b)]$$

where $b=n_t \ln[n_t/(n_t-n_p)$ and $N_o$ is the initial population of spores ($10^5$);
$n_t$ is the total number of tubes (9);
$n_p$ is the number of positive tubes.

7. Number of surviving spores: The sample containing TSB inactivated chemistry (from step 6) was diluted and plated against trypticase soy agar. The sample was incubated at 55° C. ±1° C. for two days and the number of colonies was determined.
8. Population verification: To confirm that a concentration of at least $10^6$ cfu/ml of BST was present at the start of each reaction, the stock suspension of BST ($10^7$ cfu/ml) was diluted as appropriate and plated onto trypticase soy agar pour plates (55° C., 24 hours). The colony counts were multiplied by the dilution factor to determine the final concentration BST concentration.

The data for this experiment is shown below. The results indicate that the rate of inactivation of *B. stearothermophilus* was not significantly affected as a function of increasing glucose concentration.

TABLE I

| Effect of Viscosity on the Rate of Inactivation of *B. stearothermophilus* | | | | |
|---|---|---|---|---|
| % Glucose | 0% | 1% | 10% | 20% |
| Viscosity (cp) | 1.00 | 1.03 | 1.40 | 1.91 |
| D-Value | 12.6 | 13.7 | 14.5 | 15.3 |

This data demonstrates that viscosity does not meaningfully inhibit the ability of iodide anion to serve as an effective biocidal donor molecule at a pH lower than 6.5.

Three 0.1 molar citrate-phosphate buffers (CPB) were prepared at pH values of 6.0, 6.5 and to 7.0. Experiment 4 was repeated with each of the three new CPB buffers using a single 60 minute time point in step 5 (Treatment Conditions) of the Microbiology Protocol. These measurements determined if any BST organisms survived after 60 minutes but did not determine the number of viable organisms. At a pH of 6.0 and 6.5 no organisms survived. At a pH of 7.0 there were viable organisms after 60 minutes. Experiment 4 was then repeated using pH 6.5 CPB buffer in solutions that had their viscosity adjusted to 1.03, 1.40 and 1.91 cp with glucose. Organisms were incubated for 60 minutes and samples were aseptically removed and immediately transferred to 9.5 ml neutralizing media. Samples were sonicated in a jewelry bath sonicator for 15 minutes. A one ml aliquot of each of the inactivated reaction tubes was transferred into 10 ml of TSB, incubated for 7 days at 55° C.±1° C. and observed for growth. Growth was only observed at a viscosity of 1.91 cp.

Experiment 5

The intent of this experiment is to determine the lower viscosity limit which significantly influences or eliminates the ability of donor molecules other than iodide to inactivate bacteria. Glucose was used to incrementally increase the relative viscosity.

Viscosity Measurements

The viscosity of these formulations were measured in an Ostwald viscometer by determining the amount of time it takes for the liquid level to fall through a defined length of a capillary tube with an inner diameter of 5 min. The relative viscosity of a formulation was calculated by comparing the time required for the formulation to fall divided by the time required for distilled water to fall the equivalent distance. The relative viscosity measurements were tied with a digital stopwatch and rounded off to the third significant figure. The viscosity was measured five times at each concentration of glucose and the average result was used. The measured viscosities are shown below in Table II.

TABLE II

| Viscosity of Disinfectant as a Function of Glucose | | | | | | | |
|---|---|---|---|---|---|---|---|
| % Glucose | 0 | 2.5 | 5.0 | 6.0 | 7.0 | 8.0 | 10.0 |
| Relative Viscosity (cp) | 1 | 1.03 | 1.13 | 1.16 | 1.20 | 1.22 | 1.34 |

Microbiology Protocol:

1. Organisms: *Staphlococcus aureus* (ATCC 6538).

2. Chemistry Formulations: Buffers used were 0.10 molar citrate-carbonate, pH 6.5 or 4.0; hydrogen peroxide at a final concentration of 150 ppm; horseradish peroxidase at a final concentration of 0.005 mg/ml; and the following donor molecules at the indicated final concentrations: phenol 0.001%, tyrosine 0.005% and 4-aminobenzoic acid at the indicated concentration. This experiment was repeated using the donor molecules individually at the concentrations indicated above.

3. Neutralizing media: Trypticase Soy Broth (TSB) containing 0.5% polysorbate 80. TSB has a final pH of 7.3 and is comprised of 17 grams pancreatic digest of casein; 3 grams papaic digest of soy meal; 5 grams sodium chloride; 2.5 grams glucose; 2.5 grams potassium phosphate dibasic; 1000 ml of distilled water.

4. Subculture media: Trypticase Soy Broth (TSB).

5. Treatment Conditions: At T=0 minutes, 0.1 ml of a suspension of *Staphlococcus aureus* containing 500 cfu/ml was added into 0.9 ml of disinfectant solution to yield an initial population of 50 cfu/ml. After 15 minutes, 0.5 ml of the reaction mixture was removed and immediately transferred to 4.75 ml of neutralizing media. Samples were mixed on a vortex mixer and then 2.5 ml of each sample was transferred into 7.5 ml of TSB.

6. Surviving bacteria: The sample was incubated at 37° C.±1° C. for two days and monitored visually for any signs of growth.

7. Population verification: To confirm that a concentration of at least about 50 cfu/ml of *Staphlococcus aureus* was present at the start of each reaction, 0.1 mL of the stock suspension of *Staphlococcus aureus* was plated onto trypticase soy agar pour plates (37° C., 48 hours). The colony counts were divided by the sample size (0.1) to determine the cfu/mL.

The data for this experiment at pH 6.5 is shown below in Table III. The results indicate that the ability of donor molecules other than iodide to inactivate bacteria is significantly affected above a viscosity of 1.2 cp. All samples were run in duplicate. Duplicate results agreed in all cases except for the 1.13 cp viscosity measurement. The accuracy of the viscosity measurement between the 5 and 6% glucose concentration was within the error limits of the measurement technique which indicates that the relative viscosity for these two formulations are within 0.05 cp units of each other. Therefore, the results at viscosities of 1.13 and 1.16 cp are considered ambiguous. When this experiment was repeated at a pH of 4.0 the results were identical except that there was no growth in any tubes below a pH of 1.2 cp.

TABLE III

| Growth of *Staphlococcus aureus* Versus Viscosity at pH 6.5 | | | | | | | |
|---|---|---|---|---|---|---|---|
| Relative Viscosity (cp) | 1 | 1.03 | 1.13 | 1.16 | 1.20 | 1.22 | 1.34 |
| All | No | No | Yes* | No | Yes | Yes | Yes |
| phenol | No | No | No | No | Yes | Yes | Yes |
| tyrosine | No | Yes | Yes | Yes | Yes | Yes | Yes |
| 4-amimo-benzoic acid | No | No | No | Yes | Yes | Yes | Yes |

*Results from 5% glucose concentration yielded one tube positive and one tube negative. For all other experimental conditions both results were in agreement.

What is claimed is:

1. A viscous epidermal cleaner and disinfectant for admixture with water comprising surface active agents and an antiseptic agent with said antiseptic agent consisting essentially of a peroxidase selected from the Enzyme Commission identification No. E.C. 1.11.1.7, a source of peroxide, an iodide compound which forms iodide ions upon dissolution in water, and buffering means in a concentration to cause said cleaner to have a pH in a range between about 3.0 to 6.5 in said admixture with water over a wide dilution range in which the cleaner viscosity is not less than 1.2 centipoise.

2. A viscous epidermal cleaner and disinfectant as defined in claimed 1 wherein said cleaner and disinfectant is diluted in water upon use.

3. A viscous epidermal cleaner and disinfectant as defined in claim 2 wherein said buffering means comprises buffering agent(s) selected from the group consisting of citrate, phosphate, carbonate, succinate, acetate, phthalate, arsenate, and tris (hydroxymethyl)aminomethane.

4. A viscous epidermal cleaner and disinfectant as defined in claim 3 wherein said surface active agents are selected from the class of molecules consisting of anionic, cationic, zwitterionic, non-ionic and ampholytic surface active agents including sodium lauryl sulfate, lithium lauryl sulfate, alkyl benzenesulfonates, alkane sulfonates, alkene sulfonates, Tween 20-polyoxyethylene sorbitan monolaurate, Tween 100, alkyl sulphates, alkyl ether sulphates, polyoxyethylene condensation products or primary and secondary alcohols, fatty acid amides, block polymers of ethylene oxide and propylene oxide, myristic acid, lauric acid, capric acid, caprylic acid, coconut and palm kernel fatty acids, polyethoxylated glucosides and esters, hydroxyl ethyl cellulose, hydroxy propyl quar, N-acyl-sarcosinates, sodium-N-acyl-N-methyl taurates, sodium cocoylisothioate, hydroxypropyl guar gum, amidopropyl betaines, and polyethylene glycol derivitives.

5. A viscous epidermal cleaner and disinfectant as defined in claim 4 wherein said surface active agents are selected from the group of compounds consisting of glucose, sucrose, glycerol, polyethylene glycol, polyvinyl alcohol, mineral oil, silicone glycol copolymers, triglyceride esters, acetoglyceride esters, ethoxylated glycerides, lanolin, lanolin derivitives, isopropyl lanolate, ethoxylated lanolin alcohols, polyhydric alcohols, polypropylene glycol, propylene glycol, sorbitol, polyalkylene glycols, polyalkane glycols, benzyl alcohol, methyl paraben, carboxymethyl cellulose, ethylcellulose, polyvinyl alcohol, guar gum, glycol stearates, and polyhydric alcohols.

6. A viscous epidermal cleaner and disinfectant as defined in claim 5 wherein said source of peroxide is selected from the class consisting of hydrogen peroxide, methyl peroxide, metal peroxides, percarbonates, persulphates, perphosphates, peroxyesters, urea peroxide, peroxyacids, alkylperoxides, acylperoxides, perborates and mixtures thereof.

7. A viscous epidermal cleaner and disinfectant as defined in claim 6 wherein said peroxidase is identified by the Enzyme Commission number 1.11.1.7.

8. A viscous epidermal cleaner and disinfectant as defined in claim 7 wherein said iodide compound is selected from the class of salts of iodide comprising sodium iodide, potassium iodide and other alkalai iodides.

9. A viscous epidermal cleaner and disinfectant as defined in claim 7 wherein the concentration of iodide donor is between 0.5 and 8.0 mg/mL and preferably between 1.0 and 4.0 mg/mL.

10. An epidermal cleaner disinfectant for topical application in an admixture with water consisting of a first component comprising a peroxidase and an iodide compound which forms iodide ions in water with the first component having a pH of between 7.0 and 9.0 and a second component comprising a source of hydrogen peroxide, a surfactant, and buffer agent(s) to cause a pH for the admixture of said first and second compositions in water between that of 3.0 and 6.5 and a viscosity for the admixture of at least 1.2 centipoise.

11. A viscous epidermal cleaner and disinfectant as defined in claims 1 or 2 for treatment of bovine mastitis.

12. A viscous epidermal cleaner and disinfectant as defined in claim 7 wherein the concentration of hydrogen peroxide is between 0.00 1% and 1.0% weight to volume basis in the detergent based carrier component and in a preferred range of 0.01 to 0.10%.

* * * * *